(12) United States Patent
Vitorino de Almeida et al.

(10) Patent No.: US 11,538,589 B2
(45) Date of Patent: Dec. 27, 2022

(54) IDENTIFYING ADVERSE EVENTS

(71) Applicant: KONINKLIJKE PHILIPS N.V., Eindhoven (NL)

(72) Inventors: Vanda Lúcia de Carvalho Vitorino de Almeida, Veldhoven (NL); Reinhold Wimberger-Friedl, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 176 days.

(21) Appl. No.: 16/967,342

(22) PCT Filed: Feb. 1, 2019

(86) PCT No.: PCT/EP2019/052453
§ 371 (c)(1),
(2) Date: Aug. 4, 2020

(87) PCT Pub. No.: WO2019/154721
PCT Pub. Date: Aug. 15, 2019

(65) Prior Publication Data
US 2020/0381124 A1 Dec. 3, 2020

(30) Foreign Application Priority Data
Feb. 7, 2018 (EP) .................................. 18155485

(51) Int. Cl.
*G16H 10/60* (2018.01)
*G16H 50/20* (2018.01)
(Continued)

(52) U.S. Cl.
CPC ............. *G16H 50/20* (2018.01); *G16H 10/60* (2018.01); *G16H 20/10* (2018.01); *G16H 50/30* (2018.01)

(58) Field of Classification Search
CPC ........ G16H 50/20; G16H 10/60; G16H 50/30; G16H 20/10
See application file for complete search history.

(56) References Cited

U.S. PATENT DOCUMENTS 11,049,597 B2 * 6/2021 Hanz ...................... G16H 20/10
11,145,417 B2 * 10/2021 Kheifetz ................. G16H 50/50
(Continued)

OTHER PUBLICATIONS

Donskov, et al., "Sunitib-associated hypertension and neutropenia as efficacy biomarkers in metastatic renal cell carcinoma patients", British Journal of Cancer, vol. 113, No. 11, Oct. 22, 2015, pp. 1571-1580.
(Continued)

*Primary Examiner* — Mohamed Charioui
*Assistant Examiner* — Christine Y Liao

(57) ABSTRACT

The invention discloses a system for identifying an adverse event likely to occur in respect of a subject to receive or having received immunotherapy treatment. The system comprises a memory comprising instruction data representing a set of instructions; and a processor configured to communicate with the memory and to execute the set of instructions. The set of instructions, when executed by the processor, cause the processor to obtain a subject profile associated with the subject; obtain drug administration data associated with the subject; obtain medical data associated with the subject; determine, based on the subject profile and the drug administration data, a first set (114) of adverse events likely to occur in respect of the subject; and determine, based on the subject profile and the medical data, a second set (116) of adverse events likely to occur in respect of the subject. A subject monitoring apparatus, a method and a computer program product are also disclosed.

13 Claims, 6 Drawing Sheets

| Organ System | Manifestation | Diagnostic biomarkers / indicators |
|---|---|---|
| Gastrointestinal | Immune mediated colitis Seen 5-10 weeks later typically after 2nd dose of ipilimumab. Manifests as increase in stool frequency, diarrhea or constipation, blood or mucus in stool, abdominal pain/cramping, nausea and vomiting. More common with anti-CTLA-4 therapy (30-40%). Grade 3 and 4 toxicities 1n 10% patients against 1-2% on anti-PD-1/anti-PD-L1 therapy | Complete blood count Rule out infectious and other causes Stool microscopic examination for ova, parasites and stool culture. Stool antigen for *c. difficile* if suspected clinically. Lab testing for Liver Functional tests (LFTs) and KFTs (Kidney Function Tests). Colonoscopy |
| Hepatic | Immune mediated hepatitis Appears 12-16 weeks after initiation of treatment with ipilimumab. Typically seen after the 3rd dose of checkpoint inhibitor treatment. Mostly asymptomatic elevation of liver enzyme. Fever, fatigue and jaundice may be seen in some patients. Manifests in <10% patients on anti-CTLA-4 therapy but in ~20% patients on combination (anti-CTLA-4 plus anti-PD-1/anti-PD-L1) therapy. | Complete blood count AST/ALT Total Bilirubin Rule out viral, drug induced or autoimmune causes. Monitor LFTs weekly. |
| Renal | Immune mediated Renal dysfunction Seen 14-42 weeks after initiation of treatment. | Complete blood count, Kidney Function Tests (KFTs), Urine analysis. Monitor creatinine every 2-3 days. |
| Pulmonary | Immune mediated pneumonitis Seen after 8- 14 weeks of 1st dose of ipilimumab. Asymptomatic appearance of infiltrates on lung imaging is more common. | Asymptomatic, only radiological changes. Complete blood count; Radiological imaging using high resolution computed tomography (HRCT chest). Repeat CT before every cycle. |
| Endocrine | Immune-mediated thyroiditis, adrenalitis, and hypophysitis Generally seen 9 weeks after initiation of ipilimumab treatment. | Complete blood count, Comprehensive metabolic profile. Thyroiditis: TSH, T3 and T4. Adrenalitis: ACTH, Morning serum cortisol Hypophysitis: LH/FSH/Testosterone, Prolactin. MRI brain with pituitary cuts and visual field testing if indicated. |

(51) Int. Cl.
*G16H 50/30* (2018.01)
*G16H 20/10* (2018.01)

(56) References Cited

U.S. PATENT DOCUMENTS

| | | |
|---|---|---|
| 2014/0187519 A1 | 7/2014 | Cooke et al. |
| 2015/0110779 A1 | 4/2015 | Shahabi et al. |
| 2015/0118245 A1 | 4/2015 | Weber et al. |
| 2016/0070873 A1 | 3/2016 | Huster et al. |
| 2017/0116376 A1* | 4/2017 | Fokoue-Nkoutche ............ G16H 70/40 |
| 2017/0298440 A1 | 10/2017 | Fong et al. |

OTHER PUBLICATIONS

Sobolev, et al., "Adjuvanted influenza-H1N1 vaccination reveals lymphoid signatures of age-dependent early responses and of clinical adverse events", Nature Immunology, vol. 17, No. 2, Jan. 4, 2016, pp. 204-213.

Anonymous: "Adverse event Contents", Nov. 30, 2017, 2 pages.

International Search Report and Written Opinion for International Application No. PCT/EP2019/052453, filed Feb. 1, 2019, 15 pages.

Jain, et al., "Cardiovascular Complications Associated With Novel Cancer Immunotherapies", Curr Treat Options Med (2017), 19:36, 10 pages.

Varricchi, et al., "Immune Checkpoint Inhibitors and Cardiac Toxicity: An Emerginc Issue", Current Medicinal Chemistry, 2017, 24, pp. 1-13.

Andrew, S., "Challenges of Toxicity Management in Immuno-Oncology", Journal of the National Comprehensive Cancer Network, vol. 15, No. 5.5, May 2017, pp. 706-708.

Kumar, et al., "Current Diagnosis and Management of Immune Related Adverse Events (irAEs) Induced by Immune Checkpoint Inhibitor Therapy", Frontiers in Pharmacology, Feb. 2017, vol. 8, Article 49, pp. 1-14.

\* cited by examiner

| Organ System | Manifestation | Diagnostic biomarkers / indicators |
|---|---|---|
| Gastrointestinal | Immune mediated colitis Seen 5-10 weeks later typically after 2nd dose of ipilimumab. Manifests as increase in stool frequency, diarrhea or constipation, blood or mucus in stool, abdominal pain/cramping, nausea and vomiting. More common with anti-CTLA-4 therapy (30–40%). Grade 3 and 4 toxicities 1n 10% patients against 1–2% on anti-PD-1/anti-PD-L1 therapy | Complete blood count Rule out infectious and other causes Stool microscopic examination for ova, parasites and stool culture. Stool antigen for *c. difficile* if suspected clinically. Lab testing for Liver Functional tests (LFTs) and KFTs (Kidney Function Tests). Colonoscopy |
| Hepatic | Immune mediated hepatitis Appears 12–16 weeks after initiation of treatment with ipilimumab. Typically seen after the 3rd dose of checkpoint inhibitor treatment. Mostly asymptomatic elevation of liver enzyme. Fever, fatigue and jaundice may be seen in some patients. Manifests in <10% patients on anti-CTLA-4 therapy but in ~20% patients on combination (anti-CTLA-4 plus anti-PD-1/anti-PD-L1) therapy. | Complete blood count AST/ALT Total Bilirubin Rule out viral, drug induced or autoimmune causes. Monitor LFTs weekly. |
| Renal | Immune mediated Renal dysfunction Seen 14–42 weeks after initiation of treatment. | Complete blood count, Kidney Function Tests (KFTs), Urine analysis. Monitor creatinine every 2–3 days. |
| Pulmonary | Immune mediated pneumonitis Seen after 8- 14 weeks of 1st dose of ipilimumab. Asymptomatic appearance of infiltrates on lung imaging is more common. | Asymptomatic, only radiological changes. Complete blood count; Radiological imaging using high resolution computed tomography (HRCT chest). Repeat CT before every cycle. |
| Endocrine | Immune-mediated thyroiditis, adrenalitis, and hypophysitis Generally seen 9 weeks after initiation of ipilimumab treatment. | Complete blood count, Comprehensive metabolic profile. Thyroiditis: TSH, T3 and T4. Adrenalitis: ACTH, Morning serum cortisol Hypophysitis: LH/FSH/Testosterone, Prolactin. MRI brain with pituitary cuts and visual field testing if indicated. |

Fig. 1A

IDENTIFYING ADVERSE EVENTS

RELATED APPLICATIONS

This application is the U.S. National Phase application under 35 U.S.C. § 371 of International Application No. PCT/EP2019/052453, filed on Feb. 1, 2019, which claims the benefit of European Application No. 18155485.8, filed Feb. 7, 2018. These applications are hereby incorporated by reference herein, for all purposes.

FIELD OF THE INVENTION

The invention relates to identifying adverse events and, in particular, to identifying adverse events which are likely to occur in respect of a subject receiving treatment. According to some examples, the invention relates to identifying immune-related adverse events (irAEs), which might occur in respect of a subject who is to receive, is receiving, or has received immunotherapy treatment.

BACKGROUND OF THE INVENTION

Immunotherapy involves the modification or modulation of a persons immune system in order to improve the effectiveness of the immune system to fight a disease, such as cancer. However, some cancer immunotherapies are associated with known toxicities, and may be responsible for autoimmune manifestations in some patients. For example, immunotherapy may be used in respect of inhibitory receptors such as anti-cytotoxic T-lymphocyte antigen 4 (CTLA-4) and programmed death 1 (PD-1). CTLA-4 is a checkpoint molecule which is targeted in immune checkpoint blockade therapies, and which gives a negative regulatory signal during T cell activation and supports the function of regulatory T cells. In fact, stimulating the immune response via blocking CTLA-4 with an antibody is associated with a number of autoimmune side effects, including gastrointestinal toxicity, pruritis, and fatigue. When anti-CTLA-4 is combined with anti-PD-1, enhanced anti-tumor activity comes at the cost of synergistically exacerbated toxicity, affecting a significant proportion of patients.

An immune-related adverse event (irAE) is an event which may take place in respect of a patient undergoing immunotherapy. An irAE may include a relatively mild event, such as a skin lesion, or a more serious event, such as a liver defect. In general, most irAEs are reversible and not severe. irAEs may include both induced autoimmune manifestations and other•immunological, effects such as tumor progression or paradoxical worsening of opportunistic infections, similarly observed during an immune reconstitution syndrome. Skin-related adverse events (e.g. pruritus, rush, vitiligo) are relatively common in patients, and liver and gastrointestinal events are less common.

irAEs generally occur between around 3 and 6 months after treatment initiation. However, some events, such as dermatological events, can occur as early as 5 weeks after treatment initiation, and other events may occur more than a year after treatment initiation. Some events may even occur after treatment has ended. Some effects resulting from irAEs may be irreversible if not detected and treated early. Therefore, it is important to be able to detect the onset of effects of irAEs, both during and after immunotherapy treatment. It would be desirable to identify patients at risk of suffering from an irAE, and to identify those irAEs most likely to affect a particular patient.

SUMMARY OF THE INVENTION

It would be advantageous to have a mechanism by which patients who are at risk of suffering from an adverse event, such as an immune-related adverse event, can be identified, regardless of whether the patient is planning to undergo, is currently undergoing, or has completed, immunotherapy treatment. It would also be advantageous to be able to identify those irAEs from which a particular patient is at most risk. According to the present disclosure, a system and method are provided for identifying potential adverse event based on data relating to the particular patient.

According to a first aspect, the invention provides a system for identifying an adverse event likely to occur in respect of a subject to receive or having received immunotherapy treatment, the system comprising a memory comprising instruction data representing a set of instructions; and a processor configured to communicate with the memory and to execute the set of instructions, wherein the set of instructions, when executed by the processor, cause the processor to obtain a subject profile associated with the subject; obtain drug administration data associated with the subject; obtain medical data associated with the subject; obtain toxicity data; determine, based on the subject profile, the drug administration data and the toxicity data, a first set of adverse events likely to occur in respect of the subject; and determine, based on the subject profile, the medical data and the toxicity data, a second set of adverse events likely to occur in respect of the subject.

Using such a system, it may be possible to make an early prediction or identification of an adverse event that is likely to occur in respect of a subject based on the particular details of the patient, their treatment and their medical records. Such a prediction or identification may be made without the need of a specialist medical opinion, and if a particular adverse event is identified, then a timely referral to a medical professional may be made.

In some embodiments, the set of instructions, when executed by the processor, may cause the processor to determine a third set of adverse events based on the first set of adverse events, the second set of adverse events, and the nature of the immunotherapy treatment. The subject profile may comprise at least the age of the subject and the gender of the subject. In some embodiments, the subject profile may include other information specific to the subject. The medical data may comprise at least one of a clinical history associated with the subject and a genetic profile associated with the subject.

The drug administration data may comprise details of a drug or drugs that have previously been administered to the subject, details of a drug or drugs that are currently being administered to the subject and/or details of a drug or drugs that are due or planned to be administered to the subject.

The toxicity data may comprise (i) data relating to known toxicities associated with the drugs (ii) data relating to toxicities likely to occur in subjects having medical data relevant to the subject and/or (iii) data relating to toxicities likely to occur in subjects of an age range and gender relevant to the subject.

The set of instructions, when executed by the processor, may, in some embodiments, cause the processor to determine, for at least one determined adverse event, a likelihood of occurrence of the at least one adverse event in respect of the subject.

In some embodiments, the set of instructions, when executed by the processor, cause the processor to generate an alert for delivery to at least one of the subject and a medical professional if the likelihood of occurrence of the at least one adverse event meets or exceeds a defined threshold.

The set of instructions, when executed by the processor, may cause the processor to identify at least one indicator associated with at least one determined adverse event.

In some embodiments, the adverse events may comprise immune-related adverse events (irAEs) caused by the immunotherapy treatment administered to the subject.

According to a second aspect, the invention provides a subject monitoring apparatus comprising a communications module configured to communicate with a system according to any of the preceding claims; and a detection unit configured to detect signs of one or more indicators associated with the subject, the one or more indicators being indicative of at least one adverse event determined by the system.

According to a third aspect, the invention provides a computer-implemented method for identifying an adverse event likely to occur in respect of a subject to receive or having received immunotherapy treatment, the method comprising obtaining a subject profile associated with the subject; obtaining drug administration data associated with the subject; obtaining medical data associated with the subject; determining, based on the subject profile and the drug administration data, a first set of adverse events likely to occur in respect of the subject; and determining, based on the subject profile and the medical data, a second set of adverse events likely to occur in respect of the subject.

The method may, in some embodiments, further comprise determining a third set of adverse events based on the first set of adverse events, the second set of adverse events, and the nature of the immunotherapy treatment.

According to some embodiments, the method may further comprise determining, for at least one adverse event in the determined set of adverse events, a likelihood of occurrence of the at least one adverse event in respect of the subject.

The method may further comprise generating an alert for delivery to at least one of the subject and a medical professional if the likelihood of occurrence of the at least one adverse event meets or exceeds a defined threshold.

In some embodiments, the method may further comprise identifying at least one indicator indicative of at least one determined adverse event.

According to a fourth aspect, the invention provides a computer program product comprising a non-transitory computer readable medium, the computer readable medium having computer readable code embodied therein, the computer readable code being configured such that, on execution by a suitable computer or processor, the computer or processor is caused to perform the methods disclosed herein.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 1A is a table showing examples of biomarkers and indicators for various organ systems;

DETAILED DESCRIPTION OF EMBODIMENTS

According to embodiments disclosed herein, data specific to a particular subject (e.g. a patient) may be used, and combined with other data, to determine which, if any, adverse events (e.g. immune-related adverse events, or irAEs) are likely to occur in respect of that subject. A risk score indicating a likelihood that a particular adverse event will occur may also be calculated, such that an informed decision may be made regarding which immunotherapy treatment should be provided for the subject.

Figure 1:
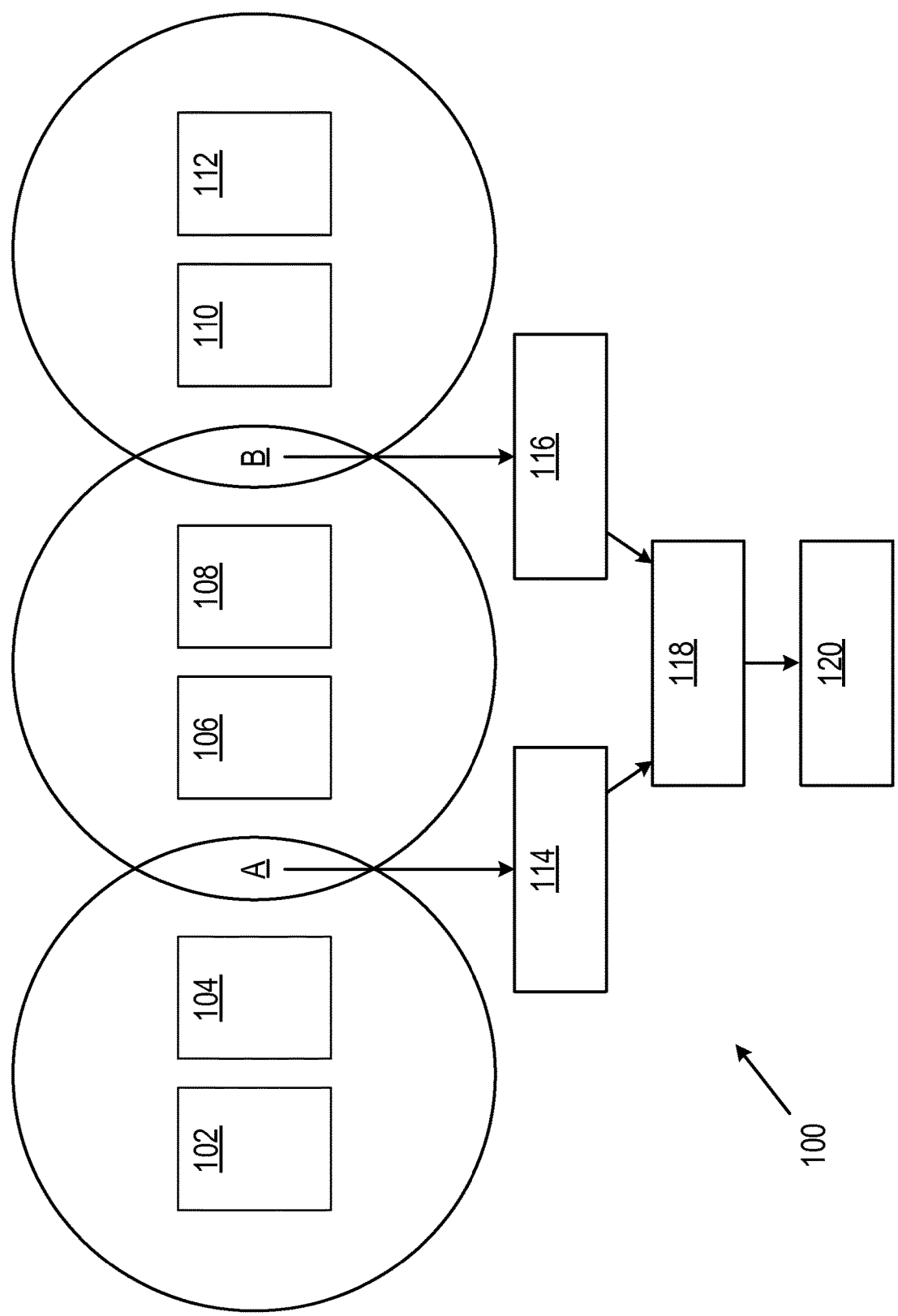
FIG. 1 is a schematic illustration of an example of a method of identifying an adverse event which may occur in respect of a subject.

Embodiments will be described with reference to an example shown in FIG. 1. It will be appreciated, however, that the following discussion is merely exemplary and that alternative examples may fall within the scope of the claims. FIG. 1 is a schematic representation of an example of a method 100 for identifying adverse events likely to occur in respect of a subject. As used herein, the term•subject, is intended to refer to a human or animal subject, and may, for example, include a patient, such as a medical patient. The method 100 involves, in a general sense, acquiring data from various sources, combining the acquired data, and generating a list of adverse events (e.g. irAEs) which are considered likely to occur in respect of the patient, based on the analysis of the data. The term•adverse event, is used herein to refer to any untoward medical occurrence in respect of a subject, as a consequence of treatment being administered to the subject. An immune-related adverse event (irAE) is a particular type of adverse event that may result from the administration of immunotherapy, in addition to or instead of other types of adverse events. Examples disclosed herein relate to immunotherapy treatments and the irAEs that may occur as a result of those treatments. However, it will be appreciated that any adverse event may be identified whether the subject is treated with immunotherapy or some other form of therapy.

According to some embodiments, data such as that represented by boxes 102 to 112 may be obtained or acquired and used to identify an adverse event. A first set of data 102 may include data relating to a treatment regime of the subject. For example, the first set of data 102 may include details of a treatment that has been administered to the subject, details of a treatment that is currently being administered to the subject and/or details of a treatment that is due or planned to be administered to the subject. In some embodiments, the data relating to a treatment regime 102 may include drug administration data. For example, the drug administration data may include details of a drug or drugs that have previously been administered to the subject, details of a drug or drugs that are currently being administered to the subject and/or details of a drug or drugs that are due or planned to be administered to the subject. In other words, the treatment regime data 102 may include details of past, current or future treatments or drug administrations (e.g. a course of drugs).

A second set of data 104 may be toxicity data, and may include data relating to known toxicities associated with the treatments or drugs included in the first set of data 102. The toxicity data may, in addition or alternatively, comprise data relating to toxicities likely to occur in subjects having medical data relevant to the subject. The toxicity data may, in addition or alternatively, comprise data relating to toxicities likely to occur in subjects of an age range and gender relevant to the subject. The second set of data 104 may, for example, be acquired from scientific or medical literature and/or from a database including details of various treatments and their known toxicities. In some examples, one or more of the toxicities associated with the treatments may include a measure of the likelihood that the toxicity will occur if the associated treatment is provided to the subject. The toxicities in the second set of data 104 may, therefore, be arranged in order of likelihood that the toxicity will occur. Some toxicities may be included in the data 104 which occur only if a particular combination of two or more treatments is provided. Similarly, the likelihood of a toxicity occurring may vary a particular combination of treatments is, or has been, provided. For example, the likelihood of a particular toxicity occurring as a result of a treatment A being administered to a patient may be relatively small. However, if a treatment B is also administered to the patient concurrently with treatment A, then the likelihood of the particular toxicity occurring may increase significantly. The set of data 104 may include details of how various combinations of the treatments or drugs included in the first set of data 102 affect the likelihood of occurrence of the toxicities included in the second set of data 104.

A third set of data 106 and a fourth set of data 108 may include details specific to the subject to be treated, and may be referred to as a subject profile. In this example, the third set of data 106 includes the subject•s age, and the fourth set of data 108 includes the gender of the subject. In some embodiments, the third and fourth sets of data 106, 108 (i.e. the subject profile) may include other personal details relating to the subject which may be included in the analysis. It should be noted, however, that the subject profile does not include medical data relating to the subject.

A fifth set of data 110 may include medical data (e.g. clinical data) associated with the subject. The medical data may include information relating to a medical history of the subject, such as medical issues suffered by the subject in the past. The medical data may include details of current or ongoing medical issues associated with the patient. The medical data included in the fifth set of data 110 may be acquired from medical records associated with the subject, such as, for example, an electronic health record (EHR). The medical data 110 generally includes information regarding the subjects health from a medical perspective.

A sixth set of data 112 may include data relating to a genetic profile of the subject. For example, a subject•s genetic profile may include data obtained from a genetic analysis of tissue samples from the subject. In some examples, the sixth set of data 112 (i.e. the genetic profile of the subject) may be grouped with the medical data associated with subject.

In some examples, data to be included in the sets of data 102 to 112 may be acquired from one or more existing data sources (e.g. databases) while, in other examples, data may be input manually, for example by a medical professional. It will also be apparent that some data relating to the subject may change over time and, therefore, one or more of the sets of data 102 to 112 may be updated which, in turn, may affect the results of any analysis of the data.

In order to determine which, if any, adverse events are likely to occur in respect of the subject based on the data included in the sets of data 102 to 112, the various sets of data may be combined in various ways. In the example shown in FIG. 1, the circles indicate how the various sets of data are combined. For example, the data 102 relating to a treatment regime of the subject and the data 104 relating to known toxicities associated with the treatment regime, optionally in combination with the data relating to toxicities likely to occur in subjects of an age range and gender relevant to the subject, may be combined with the subject profile (i.e. the third and fourth sets of data 106, 108), as indicated by the overlapping portion A. In this way, an assessment can be made of the listed toxicities (i.e. the set of data 104) in view of the age and gender of the subject. For example, from such an assessment, it may be possible to determine which of the listed toxicities are most likely to occur in a subject of a particular gender and falling within a particular age range relevant to the subject. The assessment of the datasets 102, 104 in view of the datasets 106, 108 (i.e. the subject profile) form a first set of adverse events 114 which are likely to occur in respect of the subject in view of the subject•s treatment regime, the toxicities associated with the treatments, and the subject•s age and gender. The first set of adverse events 114 may comprise a list and, in some embodiments, the first set of adverse events may be arranged in order of the likelihood of occurrence in respect of the subject.

As shown in the example of FIG. 1, the medical data 110, the data 112 relating to the genetic profile of the subject and the data relating to toxicities likely to occur in subjects having medical data relevant to the subject, optionally in combination with the data relating to toxicities likely to occur in subjects of an age range and gender relevant to the subject, may be combined with the subject profile (i.e. the third and fourth sets of data 106, 108) as indicated by the overlapping portion B. In this way, an assessment can be made of the medical (and genetic) background of the subject in view of the age and gender of the subject. For example, from such an assessment, it may be possible to determine any toxicities or other adverse events that are likely to occur in a subject of a particular gender and falling within a particular age range relevant to the subject. In this example, the gender of the subject can have a significant effect on the possible adverse events if the subject•s medical data includes any hormone-related issues. The assessment of the datasets 110, 112 in view of the datasets 106, 108 (i.e. the subject profile) form a second set of adverse events 116 which are likely to occur in respect of the subject in view of the subject•s medical background, the subject•s genetic profile, and the subject•s age and gender. As with the first set of adverse events 114, the second set of adverse events 116 may comprise a list and, in some embodiments, the second set of adverse events may be arranged in order of the likelihood of occurrence in respect of the subject.

The first and second sets of adverse events 114, 116 may be combined to create a third set of adverse events 118. In some embodiments, the third set of adverse events 118 may be determined based just on the first and second sets of adverse events 114, 116, for example by combining the first and second sets of adverse events together to form a single list. The third set of adverse events 118 may comprise a list arranged in order of the likelihood of occurrence in respect of the subject. For example, if a particular adverse event appears in both the first set of adverse events 114 and the second adverse events 116, then it may be determined that there is a relatively high likelihood that this particular adverse event will occur in respect of the subject. In some embodiments, where the adverse events in the first and second sets of adverse events 114, 116 are provided with a likelihood of occurrence (e.g. a numerical probability that they will occur in respect of the subject), then the adverse events included in the third set of adverse events 118 may be provided with a likelihood of occurrence. For example, adverse events in the sets of adverse events may be provided with a percentage value indicating the likelihood that they will occur in respect of the subject.

In some embodiments, the third set of adverse events 118 may be determined based on a combination of the first and second sets of adverse events 114, 116 and based on details of (e.g. the nature of) the immunotherapy treatment provided (or due to be provided) to the subject. Some immunotherapy treatments may carry their own risks regarding adverse events and, therefore, some immunotherapy treatments may cause the likelihood of occurrence of certain adverse events to change. Therefore, by taking into account details of the immunotherapy treatment, the third set of adverse events 118 may be even more accurate. In some embodiments, the third of adverse events may comprise a shortlist of the most relevant adverse events. For example, the shortlist may include the two or three most relevant adverse events based on the combination of the first and second sets of adverts events 114, 116 and on the details of the immunotherapy treatment being administered.

In some embodiments, a set of indicators or biomarkers 120 may be identified, which are relevant to the adverse events included in the third set of adverse events 118. In the context of the present disclosure, the detection of an indicator or biomarker may be indicative of the occurrence or possible occurrence of an adverse event. In some embodiments, the set of indicators 120 may include one or more mechanisms by which the occurrence or possible occurrence of an adverse event may be detected. The indicators included in the set of indicators 120 may, in some embodiments, be restricted by their suitability for a subject undergoing immunotherapy the particular type of immunotherapy being administered. The detection of some indicators may not be possible in a subject who is undergoing a particular form of immunotherapy.

Examples of how various adverse events may be manifested, and examples of the types of biomarkers or indicators for particular organ systems are shown in the table of FIG. 1A.

The method discussed above, and shown in FIG. 1 will now be described in the context of a particular example.

The example involves a subject for whom the following information is available:

The subject is a 63 year-old female, a former smoker of 20 packs per year (stopped smoking 5 years ago). She experienced an unintended 10 pounds (lbs) weight loss over a 3-month period The subject has been diagnosed with the non-small-cell lung carcinoma (NSCLC) stage IV disease with metastasis to the liver. The subject suffers with a cough and a shortness of breath (SOB)

Tissue analysis of the subject identified adenocarcinoma, epidermal growth factor receptor (EGFR), the ALK gene, and the ROS1 negative gene. Programmed death-ligand 1 (PD-L1) expression was <50%

A chest CT scan confirmed a primary mass in the upper lobe of the right lung, with several pleural metastases and malignant pleural effusion An MRI scan of the brain was negative for intracranial metastases The subject has not complained of blood in the sputum. The subject has a history of hypertension and hypercholesterolemia Her performance status was 1 at diagnosis The subject was started on carboplatin/paclitaxel/bevacizumab for 4 cycles. The subject showed partial response and was continued on bevacizumab until progression After two years, the subject relapsed and was switched to a treatment of immunotherapy: pembrolizumab Thus, based on the above example, the first set of data 102 may include details of the drugs that the subject has been treated with in the past and the drug that the subject is currently being treated with, namely carboplatin, paclitaxel, bevacizumab and pembrolizumab.

The second set of data 104 may include all known toxicities associated with the treatments included in the data 102, namely hypertension, proteinuria, bleeding, neutropenia, thrombocytopenia, hyponatremia, fatigue, dyspnea, cellulitis, hypothyroidism, decreased function of the adrenal gland, and inflammation of the middle tissue heart muscle. As noted above, these known toxicities may be arranged in order of likelihood of occurrence.

The third set of data 106 may include the subject•s age, namely 63, and the fourth set of data 108 may include the subject•s gender, female.

The fifth set of data 110 may include any relevant medical data available for the patient, namely that the subject has a history of hypertension, liver metastasis, pleural metastases, a malignant pleural effusion, and hypercholesterolemia.

The sixth set of data 112 may include details of any genetic data available in respect of the subject, namely that the EGFR negative gene, the ALK negative gene and the ROS1 negative gene have been identified in tissue samples taken from the subject.

By combining the first and second sets of data 102, 104 with the third and fourth sets of data 106, 108, the list of likely toxicities from the second set of data 104 can be reduced and prioritised so as to obtain the first set of adverse events 114 likely to occur in respect of the subject. In this example, the first set of adverse events 114 may include hypertension, neutropenia, fatigue, hypothyroidism, decreased function of the adrenal gland, and information of the middle tissue heart muscle.

Similarly, by combining the fifth and sixth sets of data 110, 112 with the third and fourth sets of data 106, 108, the second set of adverse events 116 likely to occur in respect of the subject can be determined. In this example, based on the available medical data and genetic data, the second set of adverse events 116 may include hypertension, inflammation of the heart muscle, fatigue, dyspnea, and muscle weakness. As noted above, the first and second sets of adverse events 114, 116 may, in some embodiments, be arranged in order of likelihood of occurrence. In some examples, the adverse events in the first and second sets 114, 116 may be provided with a numerical likelihood of occurrence, for example in the form of a percentage value.

The adverse events from the first and second sets 114, 116 may be combined to determine or generate the third set of adverse events 118. As noted above, this combination may take into account the nature of the immunotherapy treatment being provided to the subject which, in this example, is pembrolizumab. Based on the combined likelihood of occurrence of the various adverse events, and based on the effect that pembrolizumab has on the likelihood that the adverse events will occur, the third set of adverse events 118 may include hypertension and inflammation of the heart muscle, specifically, myocarditis.

From data acquired from scientific papers, literature, and other sources, the set of indicators 120 may be determined or generated. The indicators 120 in this example may include an electrocardiogram (ECG), cardiac troponin, and creatine kinase-MB (CK-MB), which is an enzyme found in heart muscle cells. Using these indicators (i.e. performing and ECG, or checking for the presence of cardiac troponin and/or CK-MB), it may be possible to detect or predict the likely occurrence of an adverse event in respect of the subject. In some instances, adverse events may be detected before the subject exhibits any symptoms. Early detection of adverse events may provide a far better outcome for the subject.

In some examples, a subject may be able to perform checks (e.g. and ECG) themselves and/or check for the presence of indicators themselves, for example at home. If any of the indicators 120 are identified or result in the positive detection of an adverse event, then a medical professional may be informed.

Figure 2:
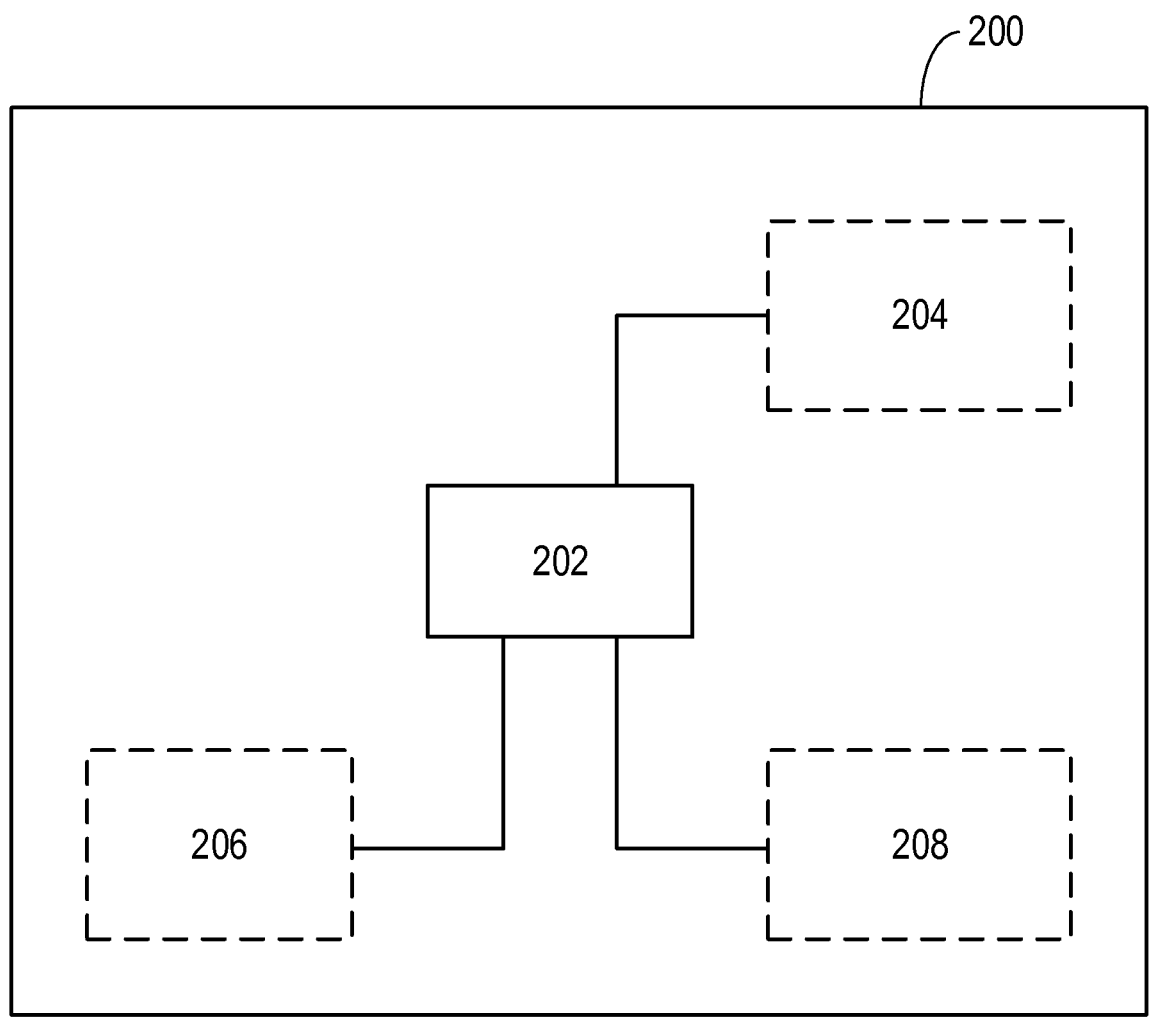
FIG. 2 is a simplified schematic of an example of a system for identifying an adverse event which may occur in respect of a subject.

The example method described above may be performed by a system, such as a computing system or suitable processing apparatus. FIG. 2 is a simplified schematic block diagram of a system 200 for identifying an adverse event likely to occur in respect of a subject to receive or having received immunotherapy treatment. The system 100 comprises a processor 202 that controls the operation of the system 200 and that can implement the methods described herein.

The system 200 further comprises a memory 206 comprising instruction data representing a set of instructions. The memory 206 may be configured to store the instruction data in the form of program code that can be executed by the processor 202 to perform the method described herein. In some implementations, the instruction data can comprise a plurality of software and/or hardware modules that are each configured to perform, or are for performing, individual or multiple steps of the method described herein. In some embodiments, the memory 206 may be part of a device that also comprises one or more other components of the system 200 (for example, the processor 202 and/or one or more other components of the system 200). In alternative embodiments, the memory 206 may be part of a separate device to the other components of the system 200.

In some embodiments, the memory 206 may comprise a plurality of sub-memories, each sub-memory being capable of storing a piece of instruction data. In some embodiments where the memory 206 comprises a plurality of sub-memories, instruction data representing the set of instructions may be stored at a single sub-memory. In other embodiments where the memory 206 comprises a plurality of sub-memories, instruction data representing the set of instructions may be stored at multiple sub-memories. For example, at least one sub-memory may store instruction data representing at least one instruction of the set of instructions, while at least one other sub-memory may store instruction data representing at least one other instruction of the set of instructions.

Thus, according to some embodiments, the instruction data representing different instructions may be stored at one or more different locations in the system 200. In some embodiments, the memory 206 may be used to store information, data (e.g. the sets of data 102 to 112), signals and measurements acquired or made by the processor 202 of the system 200 or from any other components of the system 200.

The processor 202 of the system 200 can be configured to communicate with the memory 206 to execute the set of instructions. The set of instructions, when executed by the processor 202 may cause the processor 202 to perform the methods described herein. The processor 202 can comprise one or more processors, processing units, multi-core processors and/or modules that are configured or programmed to control the system 200 in the manner described herein. In some implementations, for example, the processor 202 may comprise a plurality of (for example, interoperated) processors, processing units, multi-core processors and/or modules configured for distributed processing. It will be appreciated by a person skilled in the art that such processors, processing units, multi-core processors and/or modules may be located in different locations and may perform different steps and/or different parts of a single step of the method described herein.

Returning again to FIG. 2, in some embodiments, the system 200 may comprise at least one user interface 204. In some embodiments, the user interface 204 may be part of a device that also comprises one or more other components of the system 200 (for example, the processor 202, the memory 206 and/or one or more other components of the system 200). In alternative embodiments, the user interface 204 may be part of a separate device to the other components of the system 200.

A user interface 204 may be for use in providing a user of the system 200 (for example, a researcher such as a medical researcher, a medical professional, or any other user of a neural network model) with information (e.g. a set of adverse events 114, 116, 118 or a set of indicators 120) resulting from the method according to embodiments herein. The set of instructions, when executed by the processor 202 may cause processor 202 to control one or more user interfaces 204 to provide information resulting from the method according to embodiments herein. Alternatively or in addition, a user interface 204 may be configured to receive a user input. In other words, a user interface 204 may allow a user of the system 200 to manually enter instructions, data, or information (e.g. data from the sets of data 102 to 112). The set of instructions, when executed by the processor 202 may cause processor 202 to acquire the user input from one or more user interfaces 204.

A user interface 204 may be any user interface that enables rendering (or output or display) of information, data or signals to a user of the system 200. Alternatively or in addition, a user interface 204 may be any user interface that enables a user of the system 200 to provide a user input, interact with and/or control the system 200. For example, the user interface 204 may comprise one or more switches, one or more buttons, a keypad, a keyboard, a mouse, a mouse wheel, a touch screen or an application (for example, on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces.

In some embodiments, as illustrated in FIG. 2, the system 200 may also comprise a communications interface (or circuitry) 208 for enabling the system 200 to communicate with interfaces, memories and/or devices that are part of the system 200. The communications interface 208 may communicate with any interfaces, memories and devices wirelessly or via a wired connection.

It will be appreciated that FIG. 2 only shows the components required to illustrate this aspect of the disclosure and, in a practical implementation, the system 200 may comprise additional components to those shown. For example, the system 200 may comprise a battery or other power supply for powering the system 200 or means for connecting the system 200 to a mains power supply.

In more detail, the system 200 is configured for identifying adverse events relevant to a subject. The memory 206 comprises instruction data representing a set of instructions stop the processor 202 is configured to communicate with the memory 206 and to execute the set of instructions. The set of instructions, when executed by the processor 202 of the system 200, cause the processor to obtain a subject profile associated with the subject, obtain drug administration data associated with the subject, obtain medical data associated with the subject, obtain toxicity data, determine, based on the subject profile, the drug administration data and the toxicity data, a first set 114 of adverse events likely to occur in respect of the subject, and determine, based on the subject profile, the medical data and the toxicity data, a second set 116 of adverse events likely to occur in respect of the subject. The subject profile may be considered to include the sets of data 106 and 108, the drug administration data and toxicity data may be considered to include the sets of data 102 and 104, and the medical data may be considered to include the sets of data 110 and 112 from the example above.

As noted above, the system 200 is able to provide first and second sets of adverse events 114, 116 which are likely to occur in respect of a particular subject, based on the subject•s age and gender when combined with various other details relevant to the subject, including the subject•s medical information and details of drugs and/or treatment administered to the subject. In this way, early detection of any likely adverse events is possible, and the risks associated with the adverse events can be reduced. Moreover, since the sets of adverse events can be determined based on data relating to the subject, the determination may be performed remotely from the subject or remotely from a medical professional. This provides an additional benefit in that a medical professional is not required to examine the subject in person to identify any adverse events. Thus, the subject may be able to perform some amount of self-examination. This may lead to a reduction in medical resources, such as a medical professional•s time.

According to some embodiments, the set of instructions, when executed by the processor 202, may cause the processor to determine a third set 118 of adverse events based on the first set 114 of adverse events, the second set 116 of adverse events, and the nature of the immunotherapy treatment. In other words, the particular immunotherapy treatment being administered, or due to be administered, to the subject is taken into account so that a third, reduced set of adverse events can be generated which includes the most relevant and high-risk adverse events of those identified. Taking the immunotherapy treatment into account can be important as some immunotherapy treatments can exacerbate the effects of some adverse events.

As discussed above, the subject profile may comprise at least the age of the subject and the gender of the subject. In some embodiments, the subject profile may include other details that are specific to the subject, some of which may additionally be included in the sets of data 106 and 108, and may be taken into account when determining the adverse events likely to occur.

According to some embodiments, the medical data (e.g. the data included in the sets of data 110 and 112) may comprise at least one of a clinical history associated with the subject and a genetic profile associated with the subject. The clinical history associated with the subject may include data acquired, for example, from an electronic health record (EHR) for the subject. The genetic profile associated with the subject may include data indicating genes which have been identified in tissue samples taken from the subject.

In some examples, data may be available concerning a likelihood that a particular toxicity will result from a given treatment or drug. This likelihood (e.g. a numerical value or percentage) may be used to calculate a likelihood of occurrence for each adverse event determined by the system. Thus, in some embodiments, the set of instructions, when executed by the processor, cause the processor to determine, for at least one determined adverse event, a likelihood of occurrence of the at least one adverse event in respect of the subject. For example, the system 200 may determine that there is a 60% chance that, given the subject•s treatment regime and clinical history, the subject will suffer an adverse event in the form of hypertension. If a determine likelihood of occurrence of an adverse event is particularly high, then it may be recommended or necessary to take immediate preventative or remedial action, such as ending a particular course of treatment. Thus, the set of instructions, when executed by the processor 202, may, in some embodiments, cause the processor to generate an alert for delivery to at least one of the subject and a medical professional if the likelihood of occurrence of the at least one adverse event meets or exceeds a defined threshold. For example, a signal may be generated if it is determined that the likelihood of occurrence of any adverse event exceeds 50%.

As discussed in the example above, it may be possible to detect adverse events using appropriate indicators. For example, some indicators of adverse events may be detectable in an electrocardiogram (ECG) performed in respect of the subject. Some indicators of adverse events may be detectable in the form of biomarkers present in the blood of the subject. By performing a suitable examination of the subject (e.g. an ECG or a blood test), it may be possible to detect an indicator associated with the determined adverse events, so that any effects of the adverse events may be prevented or mitigated. Thus, in some embodiments, the set of instructions, when executed by the processor, may cause the processor to identify at least one indicator associated with at least one determined adverse event. An indicator may include a technique to be performed for identifying symptoms or evidence of an adverse event.

While examples described herein relate to identifying any kind of adverse events in respect of subject, the adverse events may, in some embodiments, comprise immune-related adverse events (irAEs) caused by the immunotherapy treatment administered to the subject.

An advantage of embodiments of this invention is that the identification of adverse events need not be performed by a medical professional. Data relating to a subject may be used by the system 200 to determine a list of any adverse events likely to occur in respect of the subject. The subject may then perform suitable procedures themselves, such as a blood test or an ECG examination, to detect any signs of the adverse events. Thus, a further aspect of the invention relates to an apparatus that may be used by subject to monitor himself or herself in order to detect symptoms of an adverse event.

Figure 3:
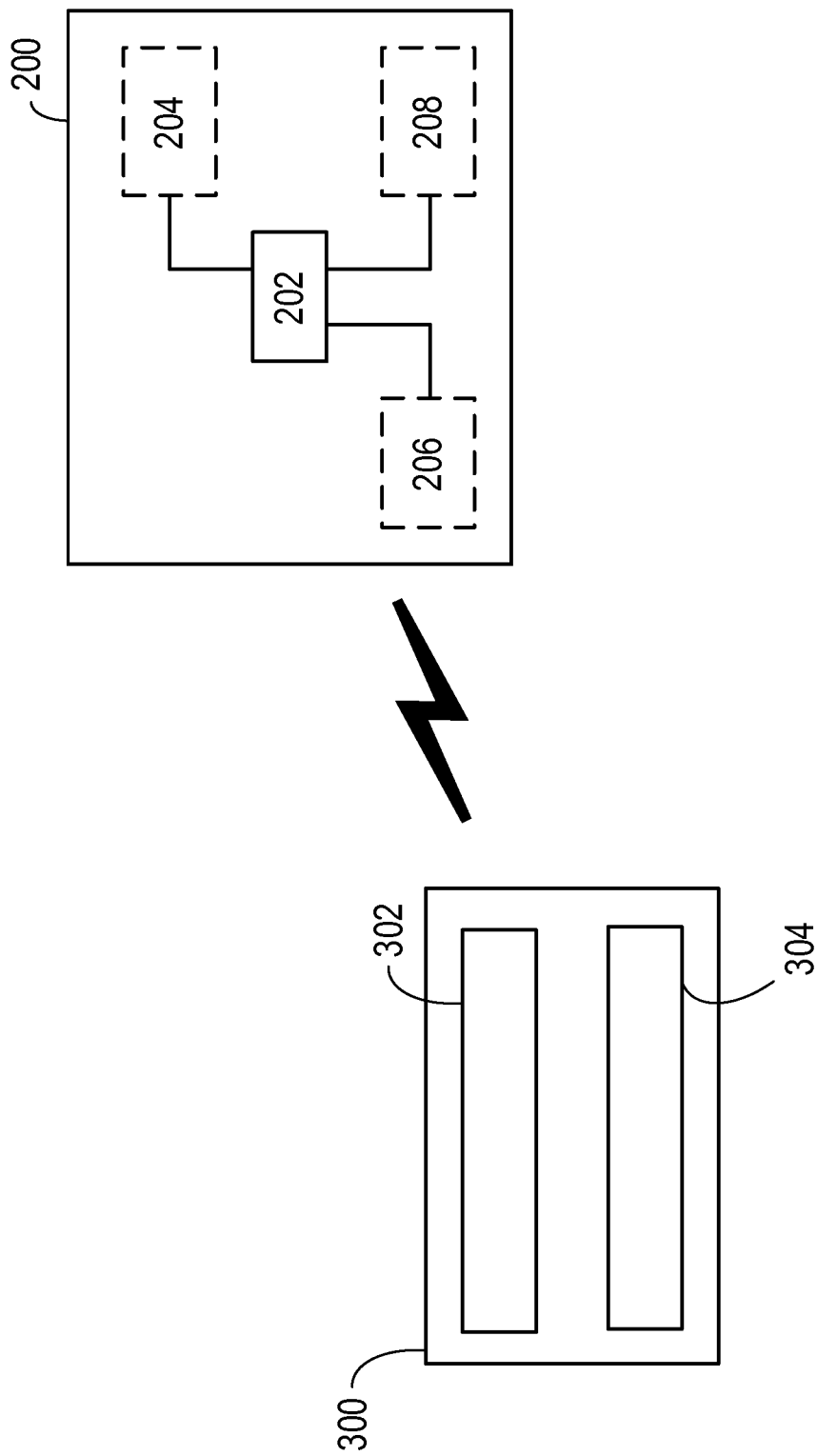
FIG. 3 is a simplified schematic of an example of a subject monitoring apparatus.

FIG. 3 is a simplified schematic of an example of a subject monitoring apparatus 300. The subject monitoring apparatus 300 comprises a communications module 302 configured to communicate with the system 200 disclosed herein. The subject monitoring apparatus 300 also comprises a detection unit 304 configured to detect signs of one or more indicators associated with the subject, the one or more indicators being indicative of at least one adverse event determined by the system. The indicators may, for example, comprise the determined set of indicators 120.

Figure 4:
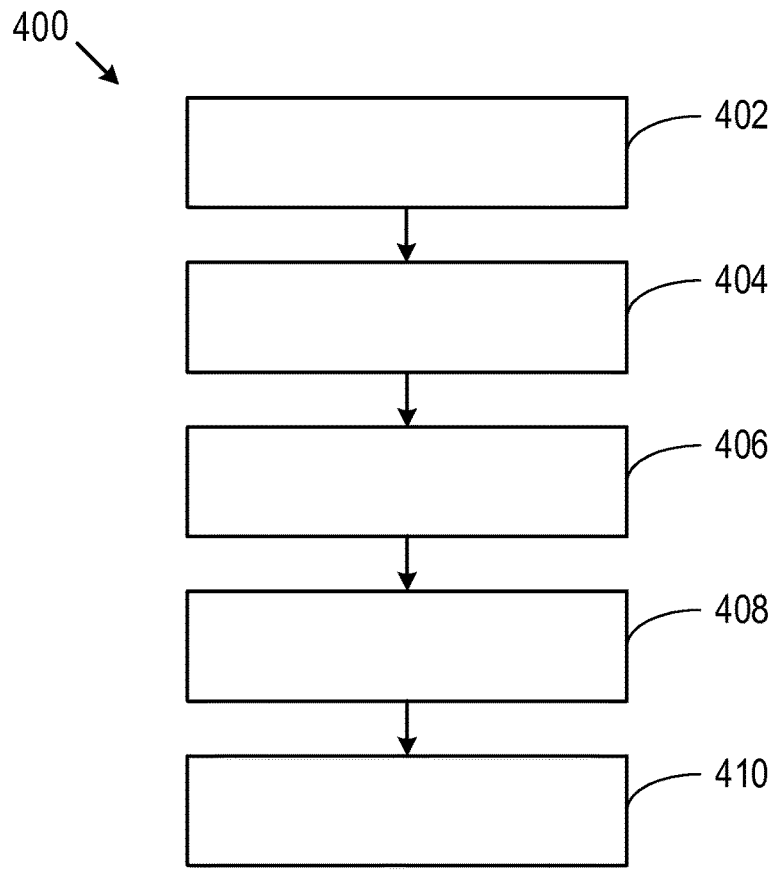
FIG. 4 is a flowchart of an example of a method for identifying an adverse event which may occur in respect of a subject.

A further aspect of the invention relates to a method for identifying adverse events. FIG. 4 is a flowchart of an example of a computer-implemented method 400 for identifying an adverse event likely to occur in respect of a subject to receive or having received immunotherapy treatment. The method 400 comprises, at step 402, obtaining a subject profile associated with the subject. As noted above, the subject profile may include data from the third and fourth sets of data 106 and 108. Specifically, the subject profile may include the age and gender of the subject. At step 404, the method 400 comprises obtaining drug administration data and toxicity data associated with the subject. The drug administration data may comprise treatment data, such as the data included in the first and second sets of data 102 and 104. As noted above, the drug administration data may include details of drugs administered to the subject previously or currently, and may include details of drugs due to be administered to the subject. The drug administration data or toxicity data may also include details of the toxicities likely to result from administering the drugs or treatments to the subject. The method 400 comprises, at step 406, obtaining medical data associated with the subject. The medical data may include historical medical or clinical data associated with the subject and current medical or clinical data associated with the subject. Since the medical data may change (e.g. new medical conditions may develop), the medical data may be updated and revised. Changes in the medical data may result in consequential changes to the outcomes of any analysis. At step 408, the method 400 comprises determining, based on the subject profile, the drug administration data and the toxicity data, a first set 114 of adverse events likely to occur in respect of the subject. At step 410, the method 400 comprises determining, based on the subject profile, the medical data and the toxicity data, a second set 116 of adverse events likely to occur in respect of the subject.

Figure 5:
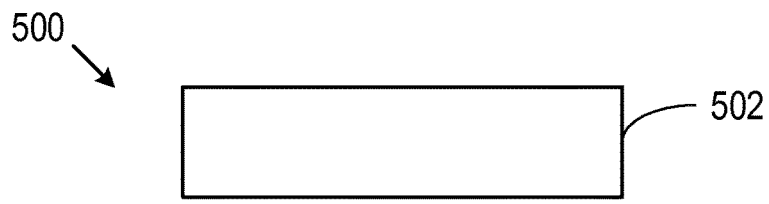
FIG. 5 is a flowchart of a further example of a method for identifying an adverse event which may occur in respect of a subject.

FIG. 5 is a flowchart of a further example of a computer-implemented method 500 for identifying an adverse event likely to occur in respect of a subject to receive or having received immunotherapy treatment. The method 500 comprises, at step 502, determining a third set 118 of adverse events based on the first set 114 of adverse events, the second set 116 of adverse events, and the nature of the immunotherapy treatment.

Figure 6:
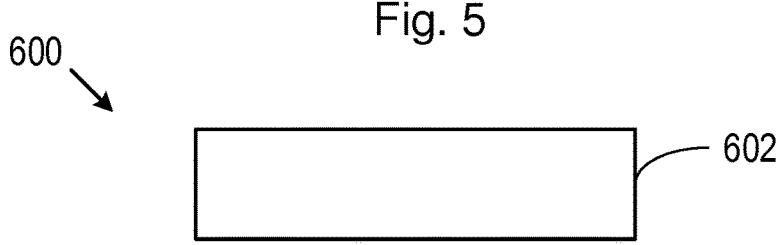
FIG. 6 is a flowchart of a further example of a method for identifying an adverse event which may occur in respect of a subject.

FIG. 6 is a flowchart of a further example of a computer-implemented method 600 for identifying an adverse event likely to occur in respect of a subject to receive or having received immunotherapy treatment. The method 600 comprises, at step 602, determining, for at least one adverse event in the determined set of adverse events, a likelihood of occurrence of the at least one adverse event in respect of the subject.

Figure 7:
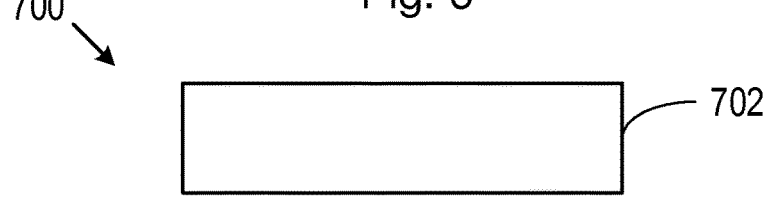
FIG. 7 is a flowchart of a further example of a method for identifying an adverse event which may occur in respect of a subject.

FIG. 7 is a flowchart of a further example of a computer-implemented method 700 for identifying an adverse event likely to occur in respect of a subject to receive or having received immunotherapy treatment. The method 700 comprises, at step 702, generating an alert for delivery to at least one of the subject and a medical professional if the likelihood of occurrence of the at least one adverse event meets or exceeds a defined threshold. In some embodiments, the defined threshold may be 50%, for example. In other examples, the defined threshold may be higher or lower, depending on the significance and/or consequences of the adverse event.

Figure 8:
FIG. 8 is a flowchart of a further example of a method for identifying an adverse event which may occur in respect of a subject.

FIG. 8 is a flowchart of a further example of a computer-implemented method 800 for identifying an adverse event likely to occur in respect of a subject to receive or having received immunotherapy treatment. The method 800 comprises, at step 802, identifying at least one indicator indicative of at least one determined adverse event. The at least one indicator may, in some embodiments, comprise a biomarker. In other examples, the at least one indicator may comprise a particular procedure, or be identified by performing a particular procedure, such as a blood test or an ECG.

In some embodiments, data determined by the methods disclosed herein (e.g. one or more determined adverse events) may be presented to a user (e.g. the subject and/or a medical professional), for example via the user interface 204.

Figure 9:
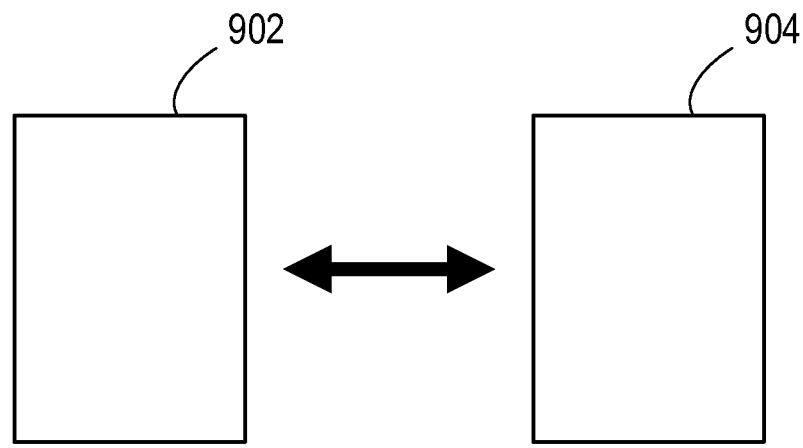
FIG. 9 is a simplified schematic of an example of a machine-readable machine and a processor.

A further aspect of the invention relates to a computer program product. FIG. 9 is a simplified schematic of an example of a processor 902 and a machine readable medium, or computer readable medium 904. The computer program product comprises a non-transitory computer readable medium 904, the computer readable medium having computer readable code embodied therein, the computer readable code being configured such that, on execution by a suitable computer or processor 902, the computer or processor is caused to perform the methods disclosed herein. The processor 902 may comprise, or be similar to, the processor 202.

The processor 202, 902 can comprise one or more processors, processing units, multi-core processors or modules that are configured or programmed to control the apparatus 200 in the manner described herein. In particular implementations, the processor 202, 902 can comprise a plurality of software and/or hardware modules that are each configured to perform, or are for performing, individual or multiple steps of the method described herein.

The term•module, as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at runtime. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

Additional aspects and embodiments are described in the following numbered paragraphs:

1. A system (200) for identifying an adverse event likely to occur in respect of a subject to receive or having received immunotherapy treatment, the system comprising:
   a memory (206) comprising instruction data representing a set of instructions; and
   a processor (202) configured to communicate with the memory and to execute the set of instructions, wherein the set of instructions, when executed by the processor, cause the processor to:
      obtain a subject profile associated with the subject;
      obtain drug administration data associated with the subject;
      obtain medical data associated with the subject;
      determine, based on the subject profile and the drug administration data, a first set (114) of adverse events likely to occur in respect of the subject; and
      determine, based on the subject profile and the medical data, a second set (116) of adverse events likely to occur in respect of the subject.

2. A system (200) according to paragraph 1, wherein the set of instructions, when executed by the processor, cause the processor to:
   determine a third set (118) of adverse events based on the first set (114) of adverse events, the second set (116) of adverse events, and the nature of the immunotherapy treatment.

3. A system (200) according to paragraph 1 or paragraph 2, wherein the subject profile comprises at least the age of the subject and the gender of the subject.

4. A system (200) according to any of the preceding paragraphs, wherein the medical data comprises at least one of a clinical history associated with the subject and a genetic profile associated with the subject.

5. A system (200) according to any of the preceding paragraphs, wherein the set of instructions, when executed by the processor, cause the processor to:
   determine, for at least one determined adverse event, a likelihood of occurrence of the at least one adverse event in respect of the subject.

6. A system (200) according to paragraph 5, wherein the set of instructions, when executed by the processor, cause the processor to:
   generate an alert for delivery to at least one of the subject and a medical professional if the likelihood of occurrence of the at least one adverse event meets or exceeds a defined threshold.

7. A system (200) according to any of the preceding paragraphs, wherein the set of instructions, when executed by the processor, cause the processor to:
   identify at least one indicator (120) associated with at least one determined adverse event.

8. A system (200) according to any of the preceding paragraphs, wherein the adverse events comprise immune-related adverse events caused by the immunotherapy treatment administered to the subject.

9. A subject monitoring apparatus (300) comprising:
   a communications module (302) configured to communicate with a system (200) according to any of the preceding paragraphs; and
   a detection unit (304) configured to detect signs of one or more indicators associated with the subject, the one or more indicators being indicative of at least one adverse event determined by the system.

10. A computer-implemented method (400) for identifying an adverse event likely to occur in respect of a subject to receive or having received immunotherapy treatment, the method comprising:
    obtaining (402) a subject profile associated with the subject;
    obtaining (404) drug administration data associated with the subject;
    obtaining (406) medical data associated with the subject;
    determining (408), based on the subject profile and the drug administration data, a first set of adverse events likely to occur in respect of the subject; and
    determining (410), based on the subject profile and the medical data, a second set of adverse events likely to occur in respect of the subject.

11. A computer-implemented method (400, 500) according to paragraph 10, further comprising:

determining (502) a third set of adverse events based on the first set of adverse events, the second set of adverse events, and the nature of the immunotherapy treatment.

12. A computer-implemented method (400, 600) according to paragraph 10 or paragraph 11, further comprising:
    determining (602), for at least one adverse event in the determined set of adverse events, a likelihood of occurrence of the at least one adverse event in respect of the subject.

13. A computer-implemented method (400, 700) according to any of paragraphs 10 to 12, further comprising:
    generating (702) an alert for delivery to at least one of the subject and a medical professional if the likelihood of occurrence of the at least one adverse event meets or exceeds a defined threshold.

14. A computer-implemented method (400, 800) according to any of paragraphs 10 to 13, further comprising:
    identifying (802) at least one indicator indicative of at least one determined adverse event.

15. A computer program product comprising a non-transitory computer readable medium (904), the computer readable medium having computer readable code embodied therein, the computer readable code being configured such that, on execution by a suitable computer or processor (902), the computer or processor is caused to perform the method of any of paragraphs 10 to 14.

The invention claimed is:

1. A system for identifying an adverse event likely to occur in respect of a subject to receive or having received immunotherapy treatment, the system comprising:
    a memory comprising instruction data representing a set of instructions; and
    a processor configured to communicate with the memory and to execute the set of instructions, wherein the set of instructions, when executed by the processor, cause the processor to:
        obtain a subject profile associated with the subject, wherein the subject profile comprises at least the age of the subject and the gender of the subject;
        obtain drug administration data associated with the subject, wherein the drug administration data comprises details of a drug or drugs that have previously been administered to the subject, details of a drug or drugs that are currently being administered to the subject and/or details of a drug or drugs that are due or planned to be administered to the subject;
        obtain medical data associated with the subject, wherein the medical data comprises at least one of a clinical history associated with the subject and a genetic profile associated with the subject;
        obtain toxicity data, wherein the toxicity data comprises (i) data relating to known toxicities associated with the drugs (ii) data relating to toxicities likely to occur in subjects having medical data relevant to the subject and/or (iii) data relating to toxicities likely to occur in subjects of an age range and gender relevant to the subject;
        determine, based on the subject profile, the drug administration data and the toxicity data, a first set of adverse events likely to occur in respect of the subject;
        determine, based on the subject profile, the medical data and the toxicity data, a second set of adverse events likely to occur in respect of the subject;
        identify at least one indicator associated with at least one determined adverse event; and
        output the at least one indicator to a user interface configured for communication with the processor such that the at least one indicator is detectable by a medical test to determine an occurrence of the least one determined adverse event.

2. A system according to claim 1, wherein the set of instructions, when executed by the processor, cause the processor to:
    determine a third set of adverse events based on the first set of adverse events, the second set of adverse events, and the nature of the immunotherapy treatment.

3. A system according to claim 1, wherein the first set of adverse events is determined based on the subject profile, the drug administration data and the toxicity data relating to known toxicities associated with the drugs and/or likely to occur in subjects of an age range and gender relevant to the subject.

4. A system according to claim 1, wherein the second set of adverse events is determined based on the subject profile, the medical data, and the toxicity data relating to toxicities likely to occur in subjects having medical data and/or of an age range and gender relevant to the subject.

5. A system according to claim 1, wherein the set of instructions, when executed by the processor, cause the processor to:
    determine, for at least one determined adverse event, a likelihood of occurrence of the at least one adverse event in respect of the subject.

6. A system according to claim 5, wherein the set of instructions, when executed by the processor, cause the processor to:
    generate an alert for delivery to at least one of the subject and a medical professional if the likelihood of occurrence of the at least one adverse event meets or exceeds a defined threshold.

7. A system according to claim 1, wherein the adverse events comprise immune-related adverse events caused by the immunotherapy treatment administered to the subject.

8. A subject monitoring apparatus comprising:
    a communications module configured to communicate with a system according to claim 1; and
    a detection unit configured to detect signs of one or more indicators associated with the subject, the one or more indicators being indicative of at least one adverse event determined by the system.

9. A computer-implemented method for identifying an adverse event likely to occur in respect of a subject to receive or having received immunotherapy treatment, the method comprising:
    obtaining a subject profile associated with the subject, wherein the subject profile comprises at least the age of the subject and the gender of the subject;
    obtaining drug administration data associated with the subject, wherein the drug administration data comprises details of a drug or drugs that have previously been administered to the subject, details of a drug or drugs that are currently being administered to the subject and/or details of a drug or drugs that are due or planned to be administered to the subject;
    obtaining medical data associated with the subject, wherein the medical data comprises at least one of a clinical history associated with the subject and a genetic profile associated with the subject;
    obtaining toxicity data, wherein the toxicity data comprises (i) data relating to known toxicities associated with the drugs (ii) data relating to toxicities likely to occur in subjects having medical data relevant to the subject and/or (iii) data relating to toxicities likely to occur in subjects of an age range and gender relevant to the subject;

determining, based on the subject profile, the drug administration data and the toxicity data, a first set of adverse events likely to occur in respect of the subject;

determining, based on the subject profile, the medical data and the toxicity data, a second set of adverse events likely to occur in respect of the subject;

identifying at least one indicator associated with at least one determined adverse event; and outputting the at least one indicator to a user interface such that the at least one indicator is detectable by a medical test to determine an occurrence of the least one determined adverse event.

10. A computer-implemented method according to claim 9, further comprising:

determining a third set of adverse events based on the first set of adverse events, the second set of adverse events, and the nature of the immunotherapy treatment.

11. A computer-implemented method according to claim 9, further comprising:

determining, for at least one adverse event in the determined set of adverse events, a likelihood of occurrence of the at least one adverse event in respect of the subject.

12. A computer-implemented method according to claim 9, further comprising:

generating an alert for delivery to at least one of the subject and a medical professional if the likelihood of occurrence of the at least one adverse event meets or exceeds a defined threshold.

13. A computer program product comprising a non-transitory computer readable medium, the computer readable medium having computer readable code embodied therein, the computer readable code being configured such that, on execution by a suitable computer or processor, the computer or processor is caused to perform the method of claim 9.

* * * * *